US00PP11941P2

(12) United States Plant Patent
Booman

(10) Patent No.: US PP11,941 P2
(45) Date of Patent: Jun. 19, 2001

(54) BEGONIA PLANT NAMED 'SAN DIEGO SUNSET'

(76) Inventor: James Lawrence Booman, 2302 Bautista Ave., Vista, CA (US) 92084

( * ) Notice: Subject to any disclaimer, the term of this patent is extended or adjusted under 35 U.S.C. 154(b) by 0 days.

(21) Appl. No.: 09/375,786

(22) Filed: Aug. 17, 1999

(51) Int. Cl.[7] ..... A01H 5/00
(52) U.S. Cl. ..... Plt./343

(58) Field of Search ..... Plt./343

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Rex Begonia plant named 'San Diego Sunset', characterized by its uniform growth habit; moderate plant vigor; no requirement for winter dormancy; and interesting and attractive leaf coloration and pattern.

1 Drawing Sheet

BACKGROUND OF THE INVENTION

The present invention relates to a new and distinct cultivar of Begonia plant, botanically know as *Begonia rex* hybrid, commercially known as Rex Begonia, and hereinafter referred to by the name 'San Diego Sunset'.

The new Rex Begonia was discovered and selected by the Inventor in a controlled environment in Vista, Calif., in August, 1995, within a large group of seedling progeny from multiple crossings of unidentified selections of *Begonia rex* hybrids.

The selection of this plant was based on its uniform growth habit, moderate plant vigor, and attractive foliage coloration and pattern.

Asexual reproduction of the new Rex Begonia by leaf cuttings taken in a controlled environment in Vista, Calif., has shown that the unique features of this new Rex Begonia are stable and reproduced true to type in successive generations.

SUMMARY OF THE INVENTION

The cultivar 'San Diego Sunset' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'San Diego Sunset'. These characteristics in combination distinguish 'San Diego Sunset' as a new and distinct Rex Begonia:

1. Uniform growth habit.
2. Moderate plant vigor.
3. Does not require winter dormancy.
4. Interesting and attractive leaf coloration and pattern.

In side-by-side comparisons conducted by the Inventor in Vista, Calif., plants of the new Rex Begonia differ from plants of the nonpatented cultivar 'Merry Christmas Corkscrew' in the following characteristics:

1. Plants of the new Rex Begonia are more compact than plants of the cultivar 'Merry Christmas Corkscrew'.

2. Leaves of plants of the new Rex Begonia are longer, more narrow, and flatter than leaves of plants of the cultivar 'Merry Christmas Corkscrew'.
3. Leaves of plants of the new Rex Begonia and the cultivar 'Merry Christmas Corkscrew' differ in coloration and pattern.
4. Leaves of plants of the new Rex Begonia do not have a "corkscrew" formation whereas leaves of plants of the cultivar 'Merry Christmas Corkscrew' have a "corkscrew" formation.
5. Plants of the new Rex Begonia do not require a winter dormancy period whereas plants of the cultivar 'Merry Christmas Corkscrew' do require a winter dormancy period.

In side-by-side comparisons conducted by the Inventor in Vista, Calif., plants of the new Rex Begonia differ from plants of the nonpatented cultivar 'Lillium' in the following characteristics:

1. Plants of the new Rex Begonia are more compact than plants of the cultivar 'Lillium'.
2. Plants of the new Rex Begonia brighter colored leaves than plants of the cultivar 'Lillium'.
3. Plants of the new Rex Begonia do not require a winter dormancy period whereas plants of the cultivar 'Lillium' do require a winter dormancy period.

BRIEF DESCRIPTION OF THE PHOTOGRAPH

The accompanying colored photograph illustrates the overall appearance of the new Rex Begonia, showing the colors as true as it is reasonably possible to obtain in colored reproductions of this type. The photograph comprises a top perspective view of a typical plant of 'San Diego Sunset'. Foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown during the spring in Vista, Calif., under conditions which approximate commercial practice. Plants used for this description were grown in 15-cm containers for about 3 months.

Botanical classification: *Begonia rex* hybrid cultivar 'San Diego Sunset.'

Commercial classification: Rex Begonia.

Parentage: Chance seedling of multiple crossings of unidentified selections of *Begonia rex* hybrids.

Propagation:

*Type*.—Leaf cuttings.

*Time to initiate roots, summer*.—About 56 days at 21° C.

*Time to initiate roots, winter*.—About 56 days at 21° C.

*Time to develop roots, summer*.—About 84 days at 21° C.

*Time to develop roots, winter*.—About 98 days at 21° C.

*Rooting habit*.—Fine, fibrous and well-branched.

Plant description:

*Plant form*.—Rosette; compact; dense and outwardly arching potted plant; freely basal branching with good leaf petiole strength.

*Vigor*.—Moderate.

*Plant height, soil surface to top of leaf canopy*.—About 22 cm.

*Plant width*.—About 48 cm.

*Leaves*.—Arrangement: Simple. Length: Petiole to apex: About 14.7 cm. Base to apex: About 18.7 cm. Width: About 13.5 cm. Shape: Oblique to ovoid. Apex: Acute. Base: Asymmetrically cordate. Margin: Pectinate; irregularly undulate. Texture: Leathery, rugose; pubescence on lower surface veins. Color: Young foliage, upper surface: Margin: Dark brown, darker than 200A. Midvein area: Velvety and darker than 200A. Blade: Pale green iridescent splotches, 138C to 147D, flushed with pink, 186C. Intermarginal: Border of green, 137A. Young foliage, lower surface: Margin: 187A shading to 183A. Midvein and lateral veins: 183A. Background: 194B. Mature, fully expanded, foliage, upper surface: Margin: Dark brown, 200A, close to 202A. Central venal areas: 200A, close to 202A. Blade: Splotches of metallic 185A to 185B and 46A; fading to 185D at apex. Background: Splotches outlined by iridescent 190C. Intermarginal: Green, 137C; spots, 185B. Veins: 200B. Mature, fully expanded, foliage, lower surface: Margin: Darker than 183A. Midvein and lateral vein areas: Darker than 183A. Background: 194B. Veins: Darker than 183A; reticulate.

*Petioles*.—Length: About 15.3 cm. Diameter: About 6.5 mm. Shape: Longitudinally grooved. Texture: Pubescent. Color: 176A to 173A.

*Stipules*.—Length: About 17.5 mm. Diameter at base: About 1.1 cm. Shape: Subulate. Color: Close to 180A.

Flower description:

*Flowering habit*.—Male flowers, single with one whorl of four tepals. Female flowers, semi-double with three tepals interior to outer whorl of five tepals. Usually about four or five flowers per cyme. Flowers persistent.

*Natural flowering season*.—Plants will flower continuously, but typically plants flower more abundantly during the spring and summer.

*Flowers*.—Shape: Rounded; somewhat cup-shaped. Diameter: About 3.5 cm. Depth (height): About 1.7 cm. Aspect: Drooping about 75° from vertical. Fragrance: None.

*Flower buds*.—Shape: Ovoid; bulbous with marginal lip. Length: About 1.5 cm. Diameter: About 1.2 cm. Color: Iridescent, 51A and 55C.

*Tepals*.—Arrangement: Rosette. Length: About 1.7 cm. Width: About 1.1 cm. Shape: Ovate with acute apex. Margin: Entire. Texture: Smooth, waxy; iridescent, translucent. Color: When opening, upper surface: 55C, hint of 55A at apex. When opening, lower surface: 55A to 55B to 55C. Fully opened, upper surface: 55C to 55D. Fully opened, lower surface: 55B to 55C.

*Peduncles*.—Angle: About 35° from vertical. Length: About 8.5 cm. Diameter: About 2.5 mm. Strength: Firm. Texture: Smooth, waxy. Color: 146C.

*Pedicels*.—Angle: About 60° from vertical. Length: About 1.6 cm. Diameter: About 2 mm. Strength: Moderate. Texture: Smooth, waxy. Color: 172B to 173C.

*Reproductive organs*.—Male flowers: Stamen quantity: About 105. Anther shape: Rhomboidal; lower sides curved inwardly. Anther length: About 2 mm. Filament length: About 1 mm. Anther color: 168B. Pollen: Not observed. Female flowers: Pistil length: About 2.2 cm. Stigma shape: Funnel; bilobate. Stigma color: 163B to 163C. Ovary: Inferior; three-winged; one large top wing and two lower wing both surfaces; 179A to 179B.

Disease resistance: Resistance to diseases common to Rex Begonia has not been determined.

Seed production: Seed production has not been observed.

It is claimed:

1. A new and distinct cultivar of Rex Begonia plant named 'San Diego Sunset', as illustrated and described.

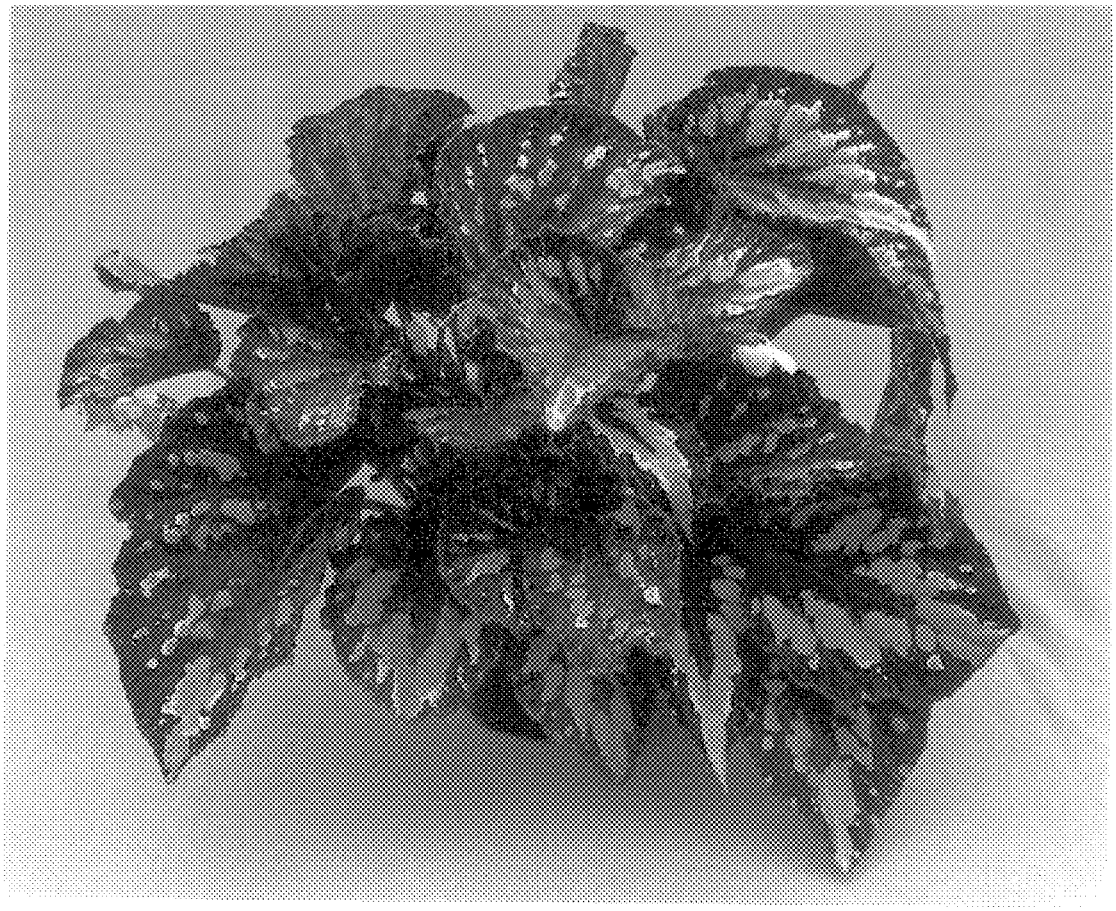

* * * * *